US010517753B2

(12) United States Patent
Miller et al.

(10) Patent No.: US 10,517,753 B2
(45) Date of Patent: Dec. 31, 2019

(54) PUBIC CATHETER APPARATUS

(71) Applicants: Stephen Henry Miller, Naples, FL (US); Jonathan Keith Jay, Naples, FL (US)

(72) Inventors: Stephen Henry Miller, Naples, FL (US); Jonathan Keith Jay, Naples, FL (US)

(73) Assignee: Jonathan Keith Jay, Naples, FL (US)

( * ) Notice: Subject to any disclaimer, the term of this patent is extended or adjusted under 35 U.S.C. 154(b) by 286 days.

(21) Appl. No.: 15/402,753

(22) Filed: Jan. 10, 2017

(65) Prior Publication Data

US 2017/0231804 A1  Aug. 17, 2017

Related U.S. Application Data

(60) Provisional application No. 62/295,599, filed on Feb. 16, 2016.

(51) Int. Cl.
*A61F 5/44* (2006.01)
*A61F 5/441* (2006.01)

(52) U.S. Cl.
CPC .......... *A61F 5/4408* (2013.01); *A61F 5/441* (2013.01); *A61F 5/4405* (2013.01); *A61M 2210/1085* (2013.01)

(58) Field of Classification Search
CPC ...... A61F 5/4405; A61F 5/4408; A61F 5/441; A61M 2210/1085; A61M 25/10
See application file for complete search history.

(56) References Cited

U.S. PATENT DOCUMENTS

| 3,780,736 | A | * | 12/1973 | Chen | A61M 3/02 137/625.47 |
| 6,129,714 | A | * | 10/2000 | Kocsi | A61F 5/44 137/511 |
| 8,974,438 | B2 | | 3/2015 | Hong et al. | |
| 2003/0032944 | A1 | * | 2/2003 | Cawood | A61F 5/44 604/544 |
| 2004/0163980 | A1 | * | 8/2004 | Tanghoj | A61F 5/44 206/363 |
| 2008/0171992 | A1 | * | 7/2008 | House | A61M 39/1011 604/180 |
| 2008/0243097 | A1 | * | 10/2008 | Goss | A41B 9/12 604/349 |
| 2010/0191183 | A1 | * | 7/2010 | Tanghoej | A61M 25/0017 604/96.01 |
| 2014/0207093 | A1 | * | 7/2014 | Marshall | A61F 5/44 604/327 |

* cited by examiner

*Primary Examiner* — Kai H Weng
(74) *Attorney, Agent, or Firm* — Dickinson Wright PLLC

(57) ABSTRACT

A pubic catheter apparatus (20) for storing a urinary catheter and drawing fluid from a bladder comprises a sanitation unit (66) defining a sanitation chamber (68) for impermeably sealing a fluid outlet (42) of the catheter from the environment when the fluid outlet (42) is disposed in the sanitation chamber (68). A support (54, 72) having a retained condition for connecting and holding the sanitation unit (66) adjacent to the body of the human and a release condition for releasing and removing the sanitation unit (66) from the body of the human. The support (54, 72) can include a belt (54) and a pouch (48) disposed thereon for surrounding and storing the sanitation unit (66), and connectors (72) in the pouch (48) having the retained condition for holding the sanitation unit (66) in the pouch (48) and the release condition for removing the sanitation unit (66) from the pouch (48).

14 Claims, 3 Drawing Sheets

PUBIC CATHETER APPARATUS

CROSS REFERENCE TO RELATED APPLICATION

This application claims the benefit of application Ser. No. 62/295,599 filed Feb. 16, 2016.

BACKGROUND OF THE INVENTION

1. Field of the Invention

A pubic catheter apparatus for storing a urinary catheter and facilitating drawing fluid from a human bladder.

2. Description of the Prior Art

Such pubic catheter apparatuses are particularly useful to patients having a physical lifestyle who experience leakage and unwanted odor. Such an apparatus is illustrated in U.S. Pat. No. 8,974,438 to Hong et al., wherein the apparatus includes a sanitation unit for impermeably sealing a fluid outlet of a urinary catheter from the environment when the fluid outlet is disposed in the sanitation chamber.

SUMMARY OF THE INVENTION

The invention provides for such a pubic catheter apparatus including a support having a retained condition for connecting and holding the sanitation unit adjacent to the body of the human and a release condition for releasing and removing the sanitation unit from the body of the human.

ADVANTAGES OF THE INVENTION

The invention in its broadest aspect provides for increased versatility, convenience, and odor control for a patient using a urinary catheter. The support eliminates the need for a urinary bag or a loose fluid outlet of a urinary catheter.

BRIEF DESCRIPTION OF THE DRAWINGS

Other advantages of the present invention will be readily appreciated, as the same becomes better understood by reference to the following detailed description when considered in connection with the accompanying drawings wherein.

DESCRIPTION OF THE ENABLING EMBODIMENT

Figure 1:
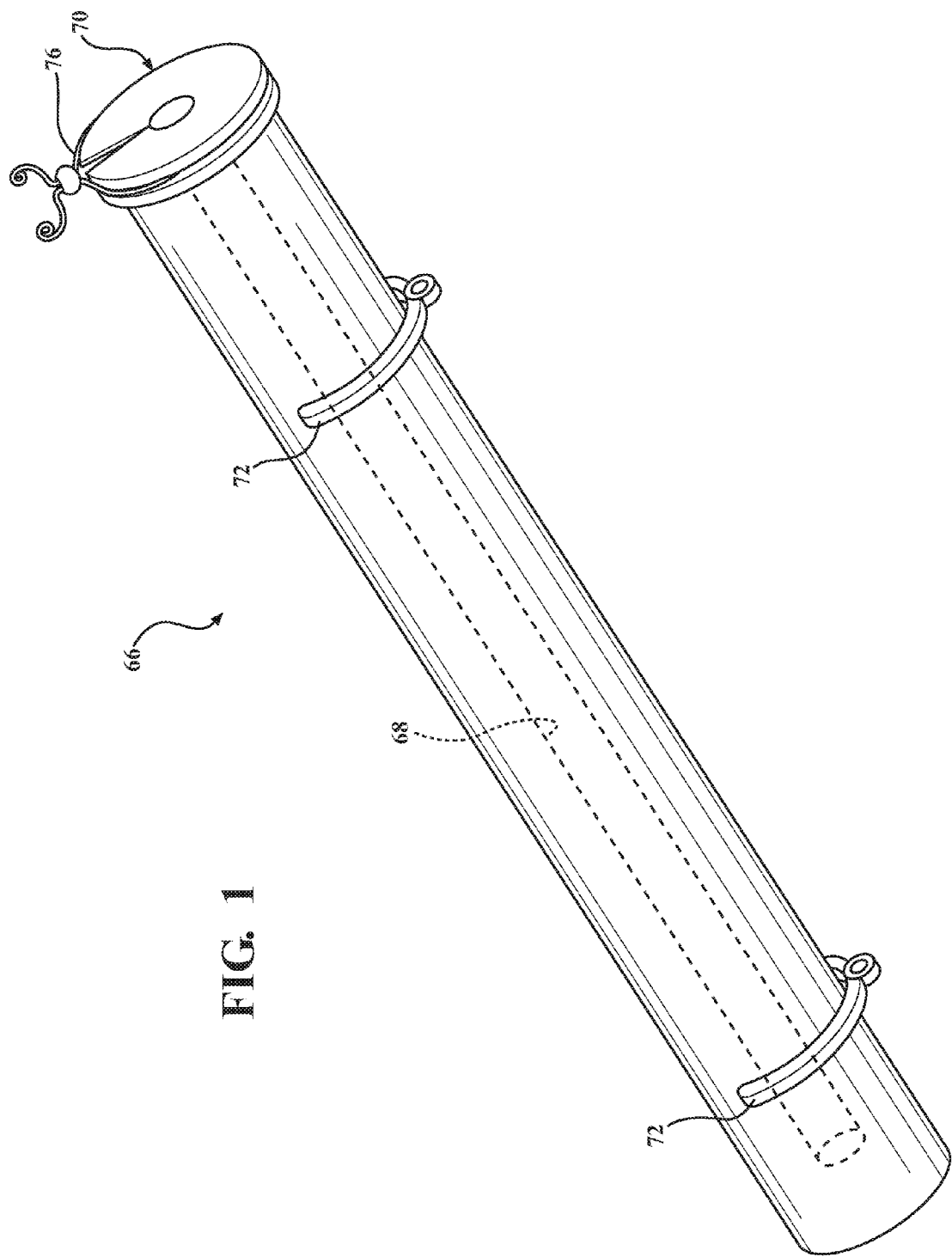
FIG. 1 is a perspective view of a sanitation unit constructed in accordance with the subject invention.
Figure 2:
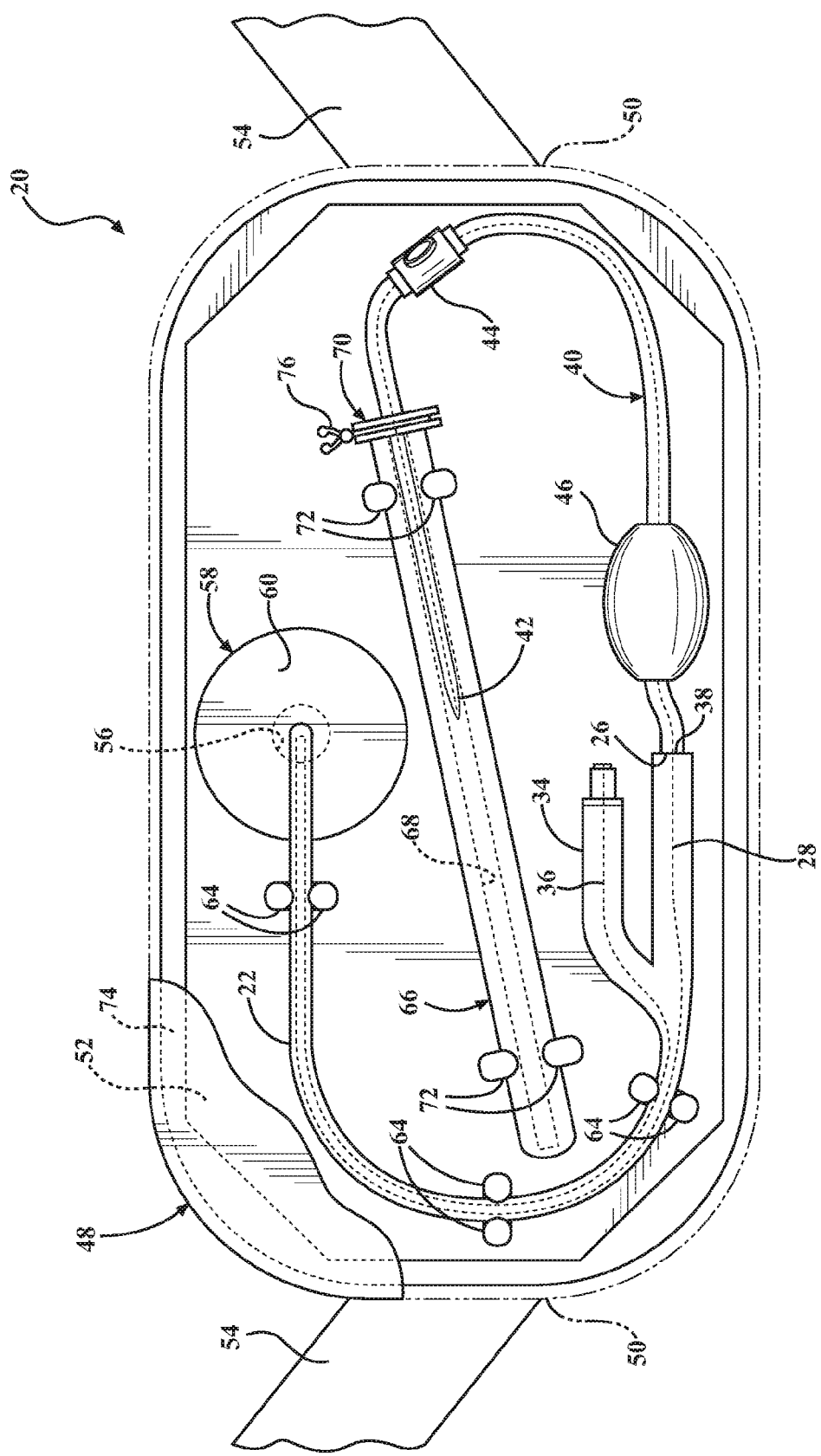
FIG. 2 is a fragmentary view of a pouch and contents stored therein.
Figure 3:
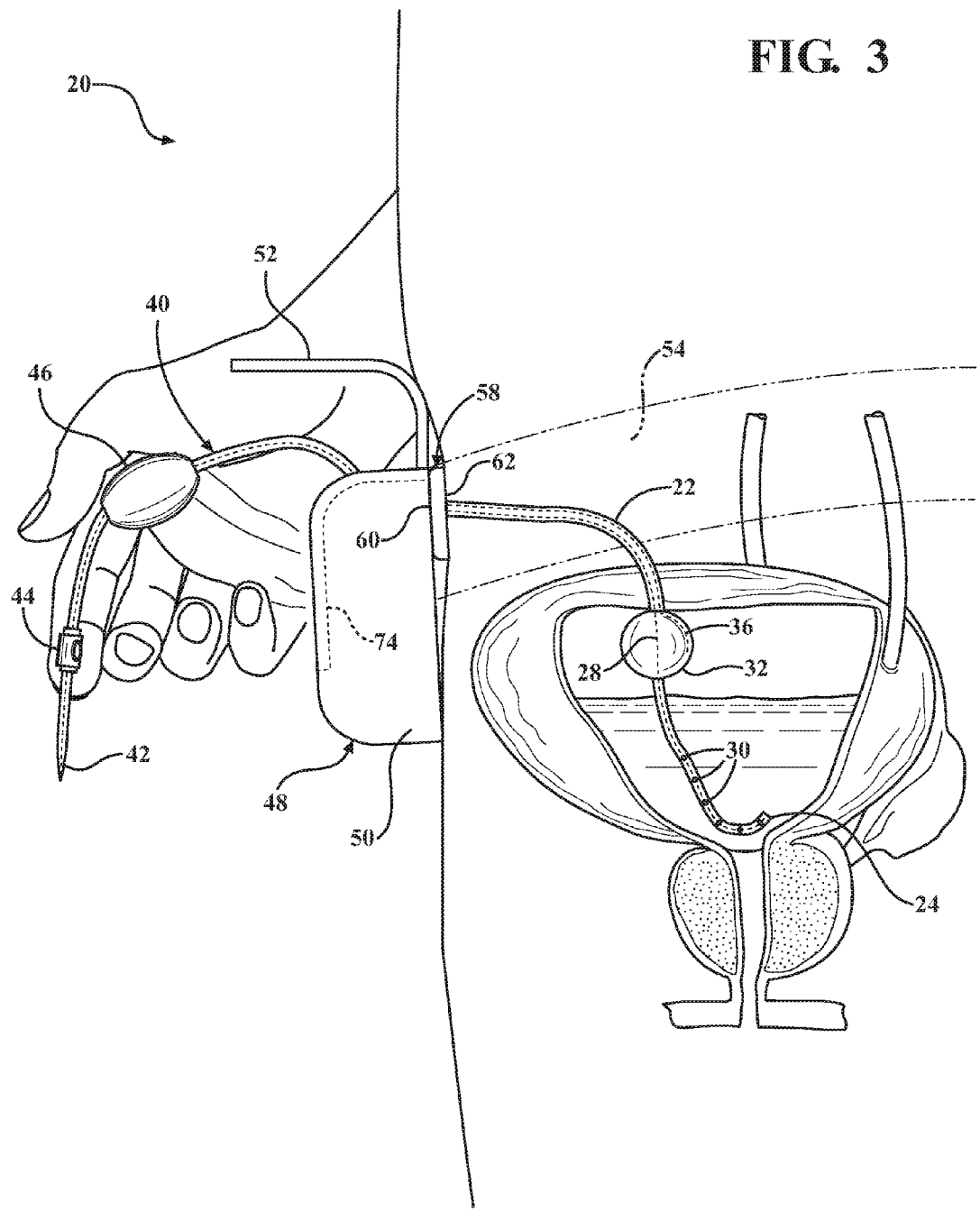
FIG. 3 is a view of the apparatus disposed on a patient.

Referring to the Figures, wherein like numerals indicate corresponding parts throughout the several views, a pubic catheter apparatus (20), generally shown, for drawing fluid from a human bladder is constructed in accordance with the subject invention shown in FIGS. 1-3.

When installed in a patient, the apparatus (20) includes a tubular member (22) having a tube-shape that extends between a proximal end (24) for insertion into the bladder of the patient and a distal end (26) for disposition outside the body of the patient. The tubular member (22) defines a first lumen passage (28) extending between the ends (24, 26) for conveying fluid from the proximal end (24) to the distal end (26). The tubular member (22) further defines a plurality of holes (30) adjacent to the proximal end (24) in fluid communication with the first lumen passage (28) for receiving fluid from the bladder.

A catheter balloon (32) is disposed along and surrounds the tubular member (22) and spaced from the holes (30) inflatable from a collapsed condition to an inflated condition for disposition against an interior wall of the bladder. The tubular member (22) includes a branch (34) having a tube-shape juxtaposed to the distal end (26) for disposition outside the patient. The tubular member (22) defines a second lumen passage (36) that extends from the branch (34) along the tubular member (22) in a side-by-side relationship with the first lumen passage (28) to the catheter balloon (32) for inflating the catheter balloon (32) from the collapsed condition to the inflated condition. The distal end (26) defines a port (38) for fluid communication with the first lumen passage (28).

A drainage conduit (40) defines a drainage passage connected to the port (38) that is in fluid communication with the first lumen passage (28) of the tubular member (22). The drainage conduit (40) extends to a fluid outlet (42) for conveying fluid from the holes (30) at the proximal end (24) through the first lumen passage (28) for discharging from the fluid outlet (42). A valve (44) is spaced from the fluid outlet (42) and has a blocked condition for preventing fluid flow through the drainage passage and an unblocked condition for allowing fluid to flow through the drainage passage of the drainage conduit (40). A pump (46) is disposed on the drainage conduit (40) on the opposite side of the valve (44) from the fluid outlet (42). The pump (46) depressurizes the drainage passage and the first lumen passage (28) of the tubular member (22) to siphon fluid through the holes (30) of the tubular member (22).

The apparatus includes a pouch (48) that extends between a pair of lateral sides (50) used for surrounding and storing the distal end (26) and the branch (34) of the tubular member (22) and the drainage conduit (40), the valve (44), and the pump (46). The pouch (48) includes a front cover (52) that is moveable between an opened condition for removing the fluid outlet (42) of the drainage conduit (40) and a closed condition for storing the drainage conduit (40). The pouch (48) also includes a belt (54) comprising a pair of straps attached to the lateral sides (50) for disposition around the body of the patient to hold the pouch (48) against the patient's body.

The pouch (48) further defines an aperture (56) for receiving the tubular member (22). The aperture (56) is sealed with a seal cap (58) that has an annular shape surrounding and slidable along the tubular member (22). The seal cap (58) includes a first side (60) for disposition against the pouch (48) and a second side (62) for disposition against the patient's body. The first side (60) and the second side (62) of the seal cap (58) each have a sealant for impermeably sealing the aperture (56) in the pouch (48) against the body of the patient, for preventing exposure of a patient's stoma. A plurality of bands (64) is disposed in the pouch (48) for respectively cradling the tubular member (22) and the drainage conduit (40). A sanitation unit (66) is disposed in the pouch (48) that has a cylindrical shape and defines a sanitation chamber (68) for impermeably sealing the fluid outlet (42) from the environment when the fluid outlet (42) is disposed in the sanitation chamber (68).

A support (54, 72) having a retained condition for connecting and holding the sanitation unit (66) adjacent to the body of the patient and a release condition for releasing and removing the sanitation unit (66) from the body of the patient. The support (54, 72) can include the belt (54) for disposition around the body of the patient. The support (54, 72) can also include the pouch (48) that surrounds and stores the sanitation unit (66). An odor agent is disposed in the sanitation chamber (68) for deodorizing the fluid outlet (42). The sanitation chamber (68) could further include absorptive material such as a sponge for containing the odor agent and absorbing any fluid still contained in the fluid outlet (42). The sanitation unit (66) includes a clasp (76) for expanding and contracting the ring seal (70) to facilitate insertion of the fluid outlet (42). The support (54, 72) may further include a plurality of connectors (72) attached to the pouch (48) having the retained condition for holding the sanitation unit (66) in the pouch (48) and the release condition for removing the sanitation unit (66) from the pouch (48). It should be appreciated that the connectors (72) could be attached to the patient's clothing without being disposed in the pouch (48).

The front cover (52) of the pouch (48) includes a seal line (74) for impermeably sealing the front cover (52) to the pouch (48) when the pouch (48) is in the closed position. The drainage conduit (40) tapers towards the fluid outlet (42) for assisting insertion into the sanitation chamber (68).

FIG. 3 illustrates the apparatus (20) disposed on the patient wherein the tubular member (22) is inserted into a stoma, or alternatively a urethra, until the distal end (26) is disposed in the bladder. In a preferred embodiment, the distal end (26) is spaced from the catheter balloon (32) so that it is disposed adjacent to the bottom of the bladder when the catheter balloon (32) is in the inflated condition and pressed against a wall of the bladder. When the tubular member (22) is fully inserted into the patient, adhesive is placed on both sides of the seal cap (58) to connect the pouch to the patient and to seal the stoma. The belt (54) is then disposed about the patient. As shown in FIG. 2, the belt contains the drainage conduit (40) and fluid outlet (42) which can be snapped into the pouch (48) until the patient needs to release urine. The pouch (48) can be worn by the patient for extended periods of time without leakage from the fluid outlet (42) because it is contained within the sanitation unit (66) which can be removed from the pouch (48) freely when the patient needs to release urine. Ideally, the patient would remove the fluid outlet (42) from the sanitation unit (66) once the fluid outlet (42) is disposed over the toilet, and the fluid outlet (42) would be placed into the sanitation unit (66) before returning back to the pouch, to eliminate any leakage into the pouch (48).

In operation, the apparatus (20) provides versatility and convenience for those who need urinary catheters. It is well understood by patients and doctors alike, that urinary catheters restrict the patient's physical movements and can also create unwanted odors. The sanitation unit (66) impermeably houses the fluid outlet (42) to prevent any unwanted odors and leakage. Furthermore, the sanitation unit (66) is attached to the patient with a belt (54) and/or a plurality of connectors (72) having a snap fit so that the movement of the patient is unhindered from a urinary bag or a loose fluid outlet (42). In addition, the sanitation unit (66) can be pulled out of the connectors (72) snap fit and placed over a toilet before removing the fluid outlet (42) to prevent leakage onto the patient after removal. While some urinary catheters have the valve (44) to prevent discharge, there are inevitably traces of urine contained in the tip of the fluid outlet (42). The sanitation unit (66) also includes a clasp (76) for expanding and contracting the ring seal (70) to facilitate insertion of the fluid outlet (42) and to maintain the impermeable seal during even the most rigorous activities. The sanitation unit (66) is disposed in the pouch (48) and the pouch (48) includes a seal line (74) for adding yet another layer of leakage and odor control. Because of the simplicity of the sanitation unit (66), it can be replaced as needed.

Obviously, many modifications and variations of the present invention are possible in light of the above teachings and may be practiced otherwise than as specifically described while within the scope of the appended claims. That which is prior art in the claims precedes the novelty set forth in the "characterized by" clause. The novelty is meant to be particularly and distinctly recited in the "characterized by" clause whereas the antecedent recitations merely set forth the old and well-known combination in which the invention resides. These antecedent recitations should be interpreted to cover any combination in which the inventive novelty exercises its utility. The use of the word "said" in the apparatus claims refers to an antecedent that is a positive recitation meant to be included in the coverage of the claims whereas the word "the" precedes a word not meant to be included in the coverage of the claims. In addition, the reference numerals in the claims are merely for convenience and are not to be read in any way as limiting.

What is claimed is:

1. A pubic catheter apparatus (20) for storing a urinary catheter and facilitating drawing fluid from a bladder of a human, the pubic catheter apparatus (20) comprising;

a tubular member (22) extending between a proximal end (24) configured to be inserted into the bladder of the human and a distal end (26) configured to be disposed outside the body of the human, said tubular member (22) defining a first lumen passage (28) extending between said ends (24, 26) for conveying fluid from said proximal end (24) to said distal end (26), said tubular member (22) defining a plurality of holes (30) adjacent to said proximal end (24) in fluid communication with said first lumen passage (28) for receiving fluid from the bladder, a catheter balloon (32) surrounding said tubular member (22) and disposed in spaced relationship from said holes (30) and inflatable from a collapsed condition to an inflated condition for disposition against an interior wall of the bladder, a drainage conduit (40) defining a drainage passage disposed in fluid communication with said first lumen passage (28) of said tubular member and extending to a fluid outlet (42) for conveying fluid from said plurality of holes (30) to said fluid outlet (42), a pouch (48) defining an aperture (56) and said tubular member (22) extending through said aperture (56) to store said distal end (26) of said tubular member (22) and said fluid outlet (42) of said drainage conduit (40) in said pouch, a sanitation unit (66) disposed in said pouch (48) and defining a sanitation chamber (68) configured to receive and impermeably seal said fluid outlet (42) of of said drainage conduit (40) from the environment when said fluid outlet (42) is disposed in said sanitation chamber (68), and a support (54, 72) having a retained condition configured to connect and hold said sanitation unit (66) adjacent to the body of the human and a release condition configured to release and remove said sanitation unit (66) from the body of the human.

2. An apparatus (20) as set forth in claim 1 wherein said support (54, 72) includes a belt (54) configured to be disposed around the body of the human.

3. An apparatus (20) as set forth in claim 2 wherein said support (54, 72) includes a plurality of connectors (72)

attached to said pouch (48) having said retained condition for holding said sanitation unit (66) in said pouch (48) and said release condition for removing said sanitation unit (66) from said pouch (48).

4. An apparatus (20) as set forth in claim 3 wherein said pouch (48) includes a front cover (52) moveable between an opened condition for removing the fluid outlet (42) and a closed condition for storing the fluid outlet (42).

5. An apparatus (20) as set forth in claim 4 wherein said front cover (52) of said pouch (48) includes a seal line (74) for impermeably sealing said front cover (52) to said pouch (48) when said pouch (48) is in said closed condition.

6. An apparatus (20) as set forth in claim 5 wherein said pouch (48) extends between a pair of lateral sides (50).

7. An apparatus (20) as set forth in claim 6 wherein said belt (54) includes a pair of straps attached to said lateral sides (50) of said pouch (48) and configured to be disposed around the body of the human to hold said pouch (48) against the body of the human.

8. An apparatus (20) as set forth in claim 1 wherein said drainage conduit (40) includes a valve (44) spaced from said fluid outlet (42) having a blocked condition for preventing fluid flow through said drainage passage and an unblocked condition for allowing fluid to flow through said drainage conduit (40).

9. An apparatus (20) as set forth in claim 8 wherein said drainage conduit (40) includes a pump (46) disposed on said drainage conduit (40) on the opposite side of said valve (44) from said fluid outlet (42) for depressurizing said drainage passage.

10. An apparatus (20) as set forth in claim 9 wherein said drainage conduit (40) tapers towards said fluid outlet (42) for into said sanitation chamber (68).

11. An apparatus (20) as set forth in claim 1 wherein said sanitation unit (66) includes a ring seal (70) for maintaining said impermeable seal.

12. An apparatus (20) as set forth in claim 11 wherein said sanitation unit (66) includes a clasp (76) for expanding and contracting said ring seal (70) to facilitate insertion of the fluid outlet (42).

13. An apparatus (20) as set forth in claim 1 wherein said sanitation unit (66) includes an odor agent disposed in said sanitation chamber (68) for deodorizing the fluid outlet (42).

14. A pubic catheter apparatus (20) for storing a urinary catheter and facilitating drawing fluid from a bladder of a human, the pubic catheter apparatus (20) comprising;
a tubular member (22) having a tube-shape extending between a proximal end (24) configured to be inserted into the bladder of the human and a distal end (26) configured to be disposed outside the body of the human,
said tubular member (22) defining a first lumen passage (28) extending between said ends (24, 26) for conveying fluid from said proximal end (24) to said distal end (26),
said tubular member (22) defining a plurality of holes (30) adjacent to said proximal end (24) in fluid communication with said first lumen passage (28) for receiving fluid from the bladder,
a catheter balloon (32) surrounding said tubular member (22) and spaced from said holes (30) and inflatable from a collapsed condition to an inflated condition for disposition against an interior wall of the bladder,
said tubular member (22) including a branch (34) having a tube-shape juxtaposed to said distal end (26),
said tubular member (22) defining a second lumen passage (36) extending from said branch (34) along said tubular member (22) in a side-by-side relationship with said first lumen passage (28) to said catheter balloon (32) for inflating said catheter balloon (32) from said collapsed condition to said inflated condition,
said distal end (26) defining a port (38) for fluid communication with said first lumen passage (28),
a drainage conduit (40) defining a drainage passage connected to said port (38) in fluid communication with said first lumen passage (28) of said tubular member (22) and extending to a fluid outlet (42) for conveying fluid from said holes (30) at said proximal end (24) through said first lumen passage (28) and discharging from said fluid outlet (42),
a valve (44) spaced from said fluid outlet (42) having a blocked condition for preventing fluid flow through said drainage passage and an unblocked condition for allowing fluid to flow through said drainage conduit (40),
a pump (46) disposed on said drainage conduit (40) on the opposite side of said valve (44) from said fluid outlet (42) for depressurizing said drainage passage and said first lumen passage (28) of said tubular member (22) to siphon fluid through said holes (30) of said tubular member (22),
a pouch (48) extending between a pair of lateral sides (50) and surrounding and storing said distal end (26) and said branch (34) of said tubular member (22) and said drainage conduit (40) and said valve (44) and said pump (46),
said pouch (48) including a front cover (52) moveable between an opened condition for removing said fluid outlet (42) of said drainage conduit (40) and a closed condition for storing said drainage conduit (40),
said pouch (48) including a belt (54) comprising a pair of straps attached to said lateral sides (50) of said pouch (48) and configured to be disposed around the body of the human and hold said pouch (48) against the body of the human,
said pouch (48) further defining an aperture (56),
said tubular member (22) extending through said aperture (56),
a seal cap (58) having an annular shape surrounding and slidable along said tubular member (22),
said seal cap (58) including a first side (60) for disposition against said pouch (48) and a second side (62) configured to be disposed against the body of the human,
said first side (60) and said second side (62) of said seal cap (58) each having a sealant for impermeably sealing said aperture (56) in said pouch (48),
a plurality of bands (64) disposed in said pouch (48) for respectively cradling said tubular member (22) and said drainage conduit (40),
a sanitation unit (66) disposed in said pouch (48) having a cylindrical shape and defining a sanitation chamber (68) for impermeably sealing said fluid outlet (42) from the environment when said fluid outlet (42) is disposed in said sanitation chamber (68),
a support (54, 72) having a retained condition configured to connect and hold said sanitation unit (66) adjacent to the body of the human and a release condition configured to release and remove said sanitation unit (66) from the body of the human,
said support (54, 72) including said belt (54) configured to be disposed around the body of the human,
said support (54, 72) including said pouch (48) surrounding and storing said sanitation unit (66), an odor agent disposed in said sanitation chamber (68) for deodorizing said fluid outlet (42),
a seal ring (70) disposed on said sanitation unit (66) for engaging and holding said fluid outlet (42) in said sanitation chamber (68) and maintaining the impermeable seal,
said sanitation unit (66) including a clasp (76) for expanding and contracting said ring seal (70) to facilitate insertion of the fluid outlet (42),
said support (54, 72) including a plurality of connectors (72) attached to said pouch (48) having said retained condition for holding said sanitation unit (66) in said pouch (48) and said release condition for removing said sanitation unit (66) from said pouch (48),
said front cover (52) of said pouch (48) including a seal line (74) for impermeably sealing said front cover (52) to said pouch (48) when said pouch (48) is in said closed position,
said drainage conduit (40) tapering towards said fluid outlet (42) for insertion into said sanitation chamber (68).

\* \* \* \* \*